United States Patent [19]
Janicki et al.

[11] Patent Number: 6,140,348
[45] Date of Patent: *Oct. 31, 2000

[54] TREATING/PREVENTING HEART FAILURE VIA INHIBITION OF MAST CELL DEGRANULATION

[75] Inventors: Joseph Janicki; Gregory L. Brower, both of Auburn, Ala.

[73] Assignee: Auburn University, Auburn, Ala.

[*] Notice: This patent is subject to a terminal disclaimer.

[21] Appl. No.: 09/375,372

[22] Filed: Aug. 17, 1999

Related U.S. Application Data

[63] Continuation-in-part of application No. 09/156,759, Sep. 18, 1998, Pat. No. 5,952,353.
[60] Provisional application No. 60/059,568, Sep. 19, 1997.

[51] Int. Cl.[7] .............................................. A61K 31/4535
[52] U.S. Cl. ............................................................ 514/324
[58] Field of Search ............................................. 514/324

[56] References Cited

U.S. PATENT DOCUMENTS

| | | | |
|---|---|---|---|
| 4,474,787 | 10/1984 | Cairns et al. | 424/258 |
| 4,918,078 | 4/1990 | Brown et al. | 514/291 |
| 4,935,244 | 6/1990 | Clark | 424/450 |
| 5,049,389 | 9/1991 | Radhakrishnan | 424/450 |
| 5,474,983 | 12/1995 | Kuna et al. | 514/12 |
| 5,629,322 | 5/1997 | Guthikonda et al. | 514/313 |

FOREIGN PATENT DOCUMENTS

97/15284   5/1997   WIPO .

OTHER PUBLICATIONS

Berges et al., Intensivmedizin, 18/4, (229–231) (abstract), 1981.

Kovanen et al, Circulation, vol. 92, pp. 1084–1088 (1995).

Craps, J. Allergy Clin. Immunol., pp. 389–393 (Aug. 1985).

Primary Examiner—Phyllis G. Spivack
Attorney, Agent, or Firm—Burns, Doane, Swecker & Mathis, L.L.P.

[57] ABSTRACT

Heart failure is treated/prevented by administering to candidate subjects the inhibitor of mast cell degranulation ketotifen to prevent adverse myocardial remodeling secondary to a sustained blood volume overload.

3 Claims, 9 Drawing Sheets

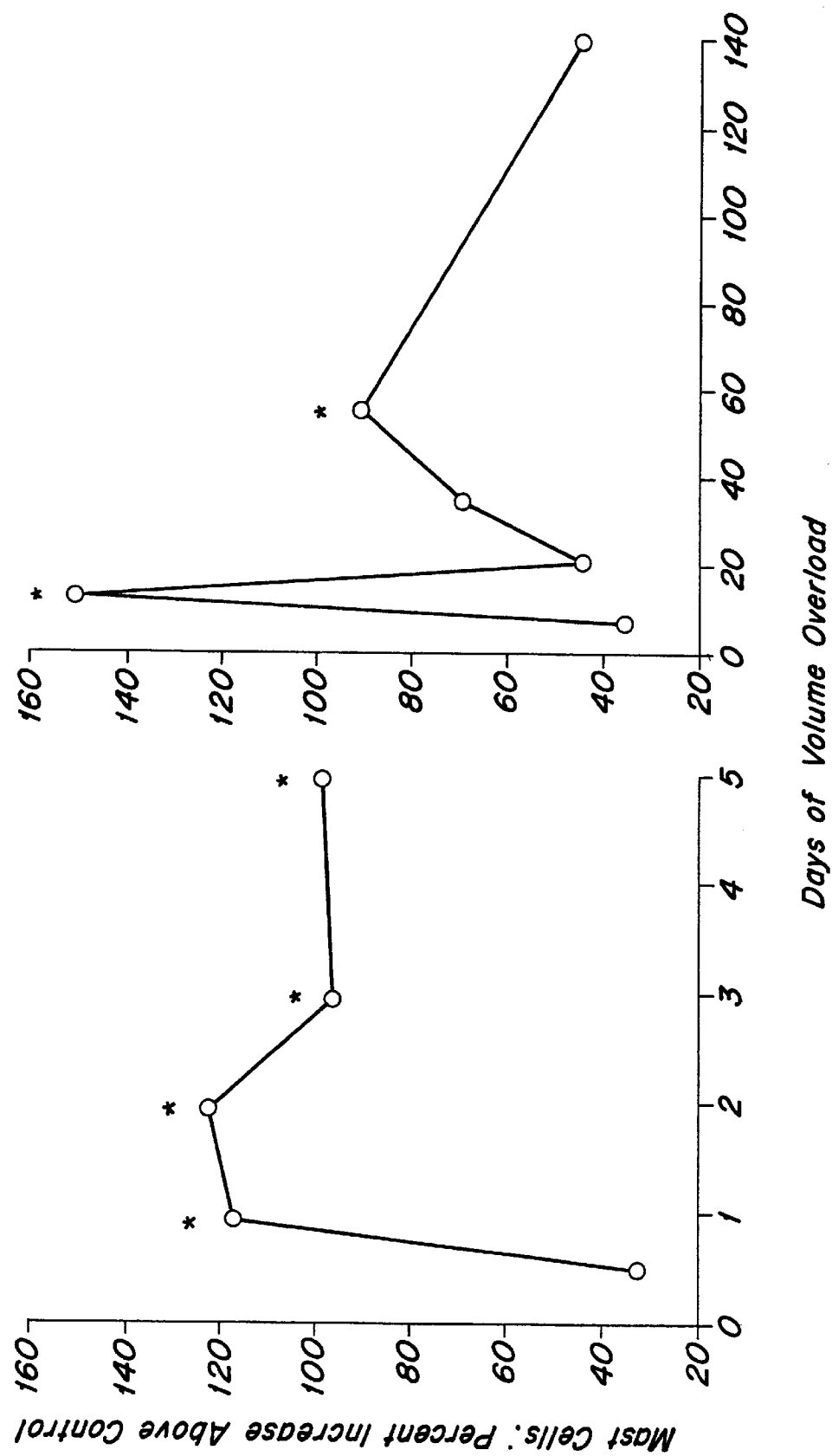

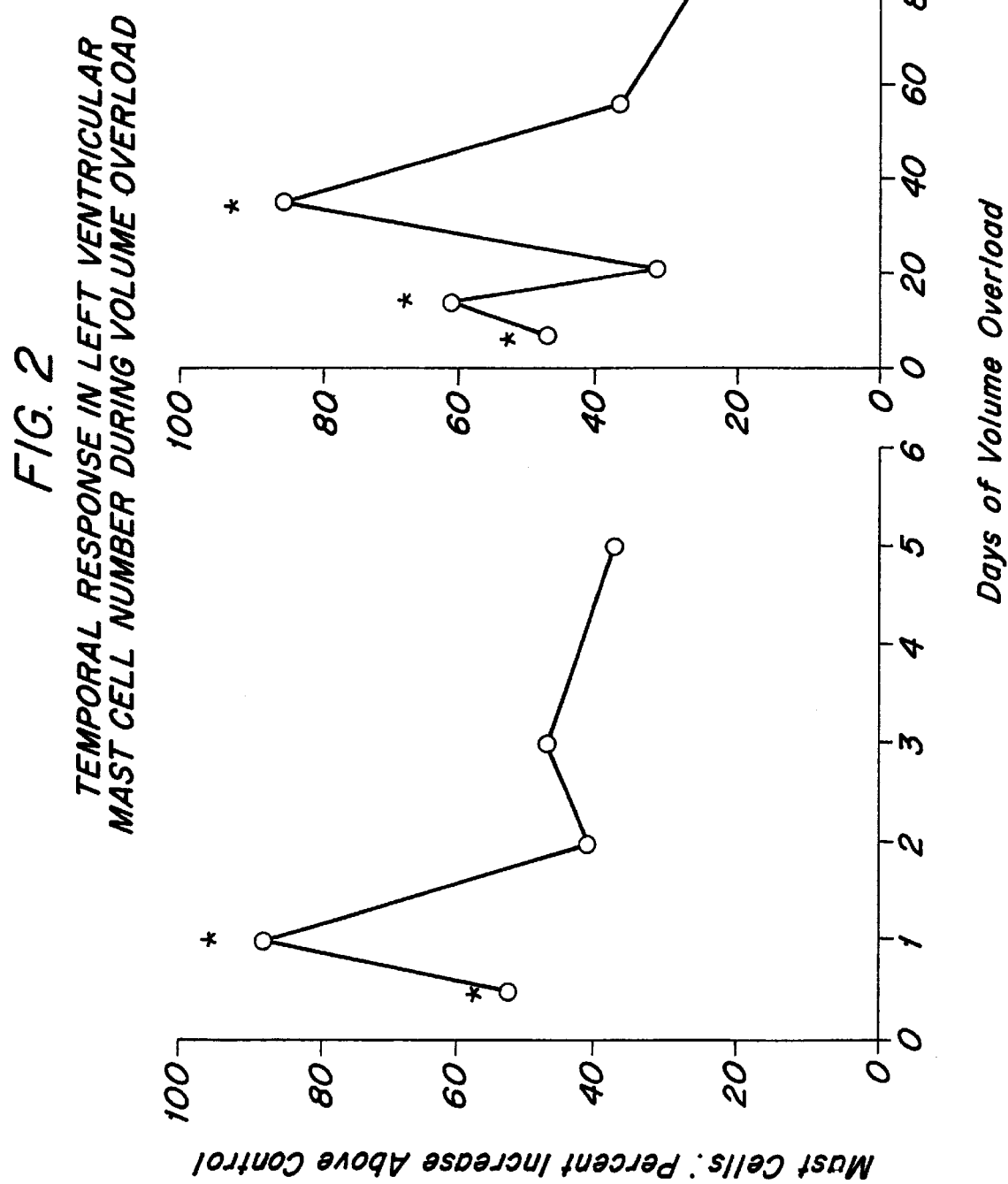

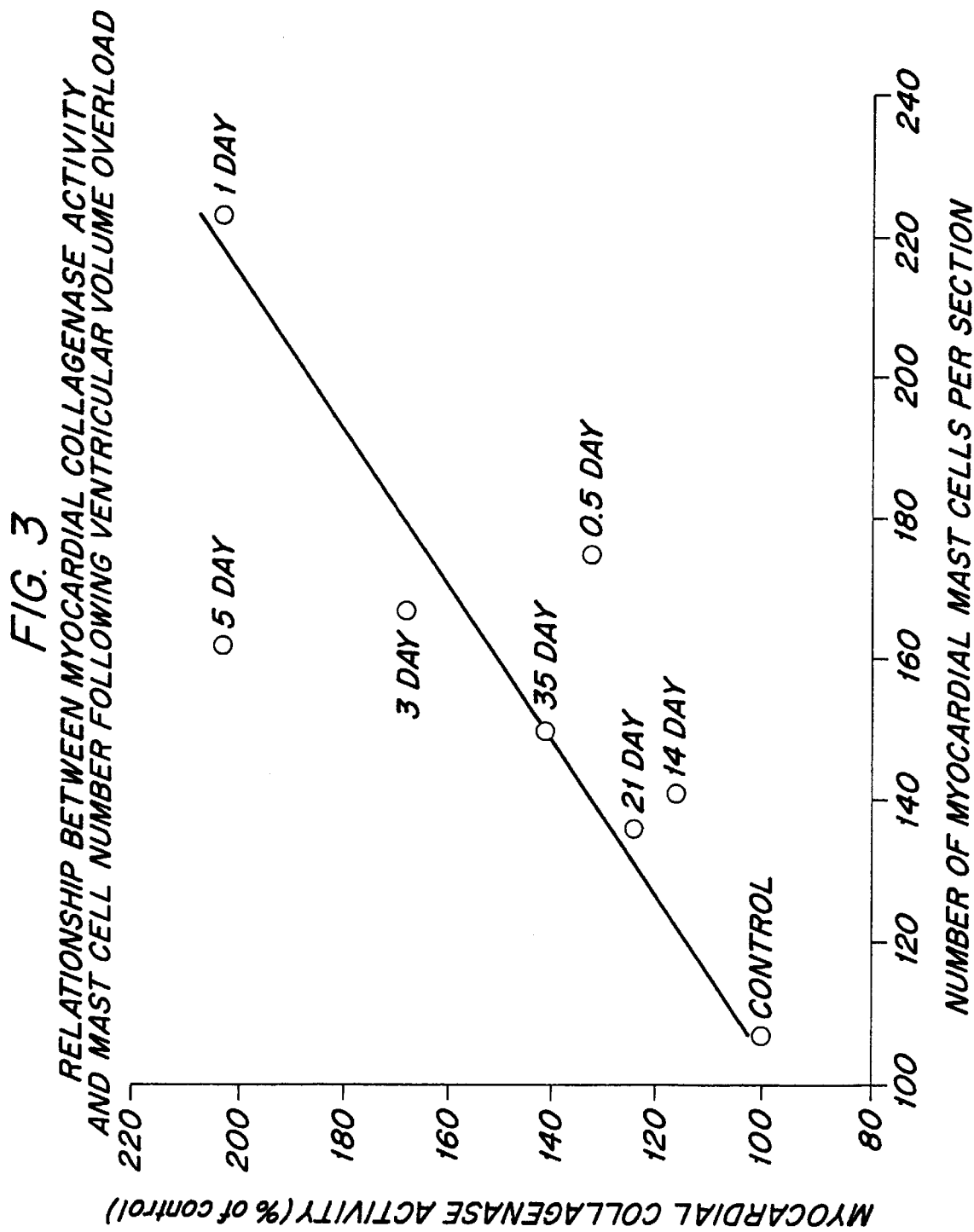

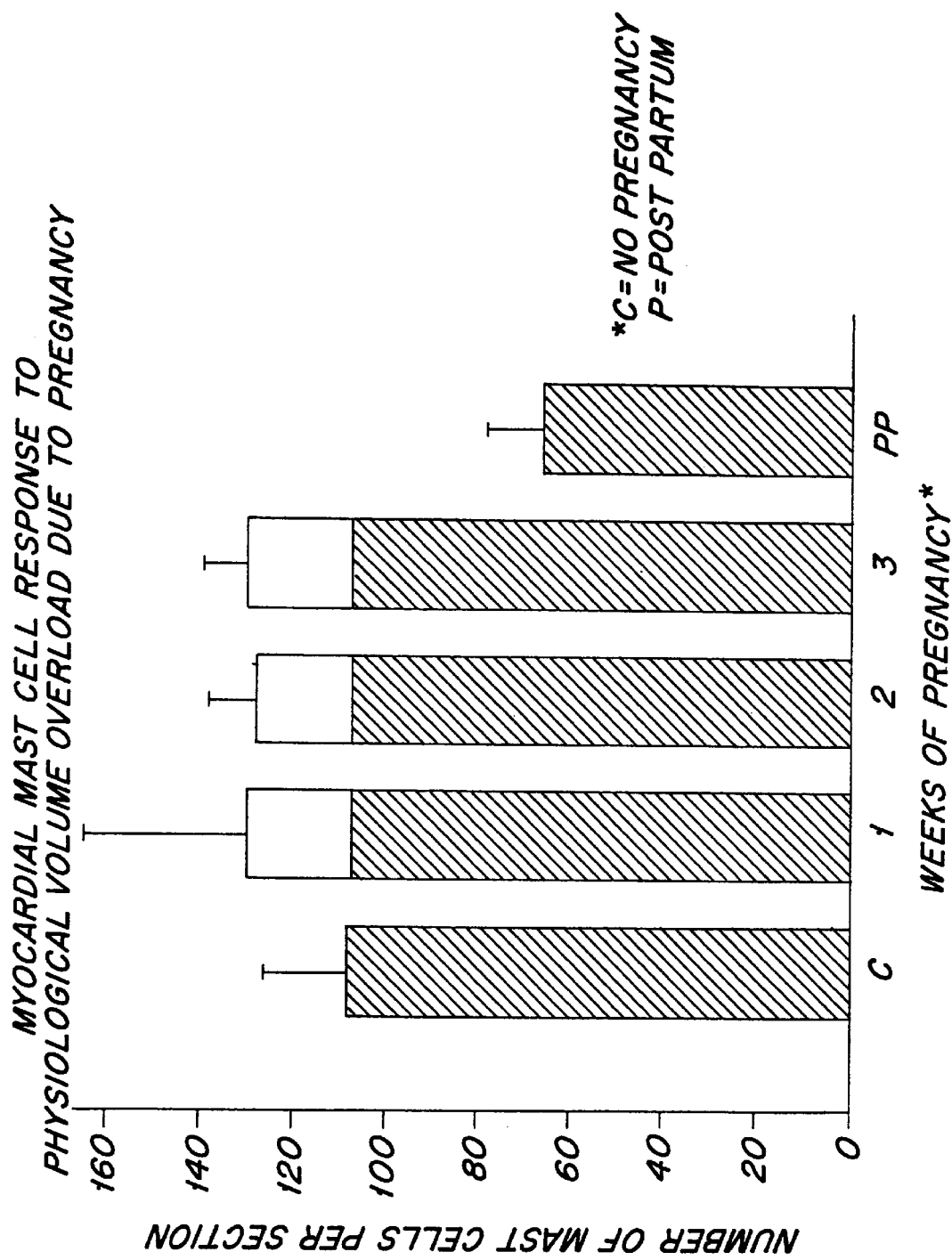

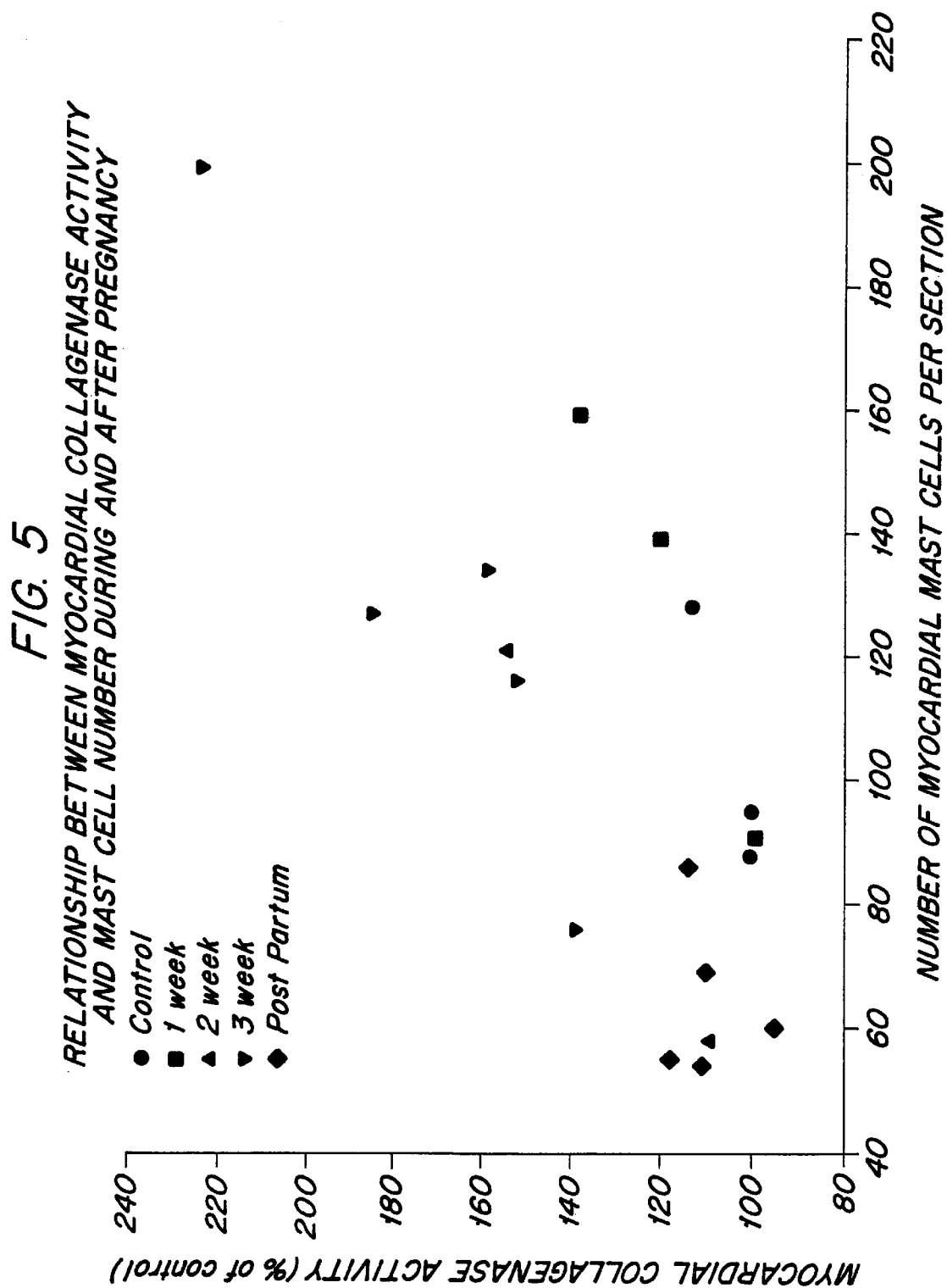

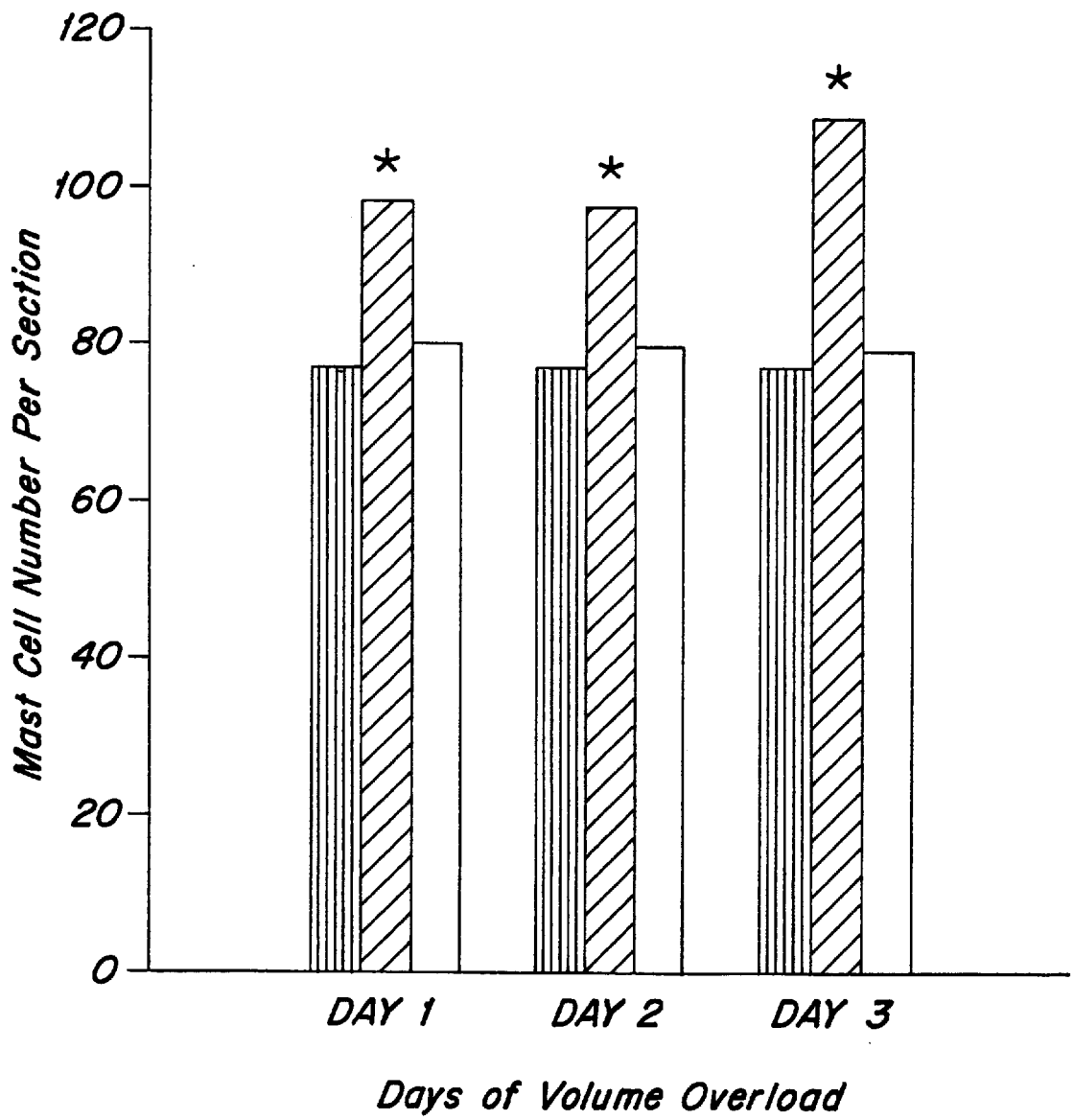

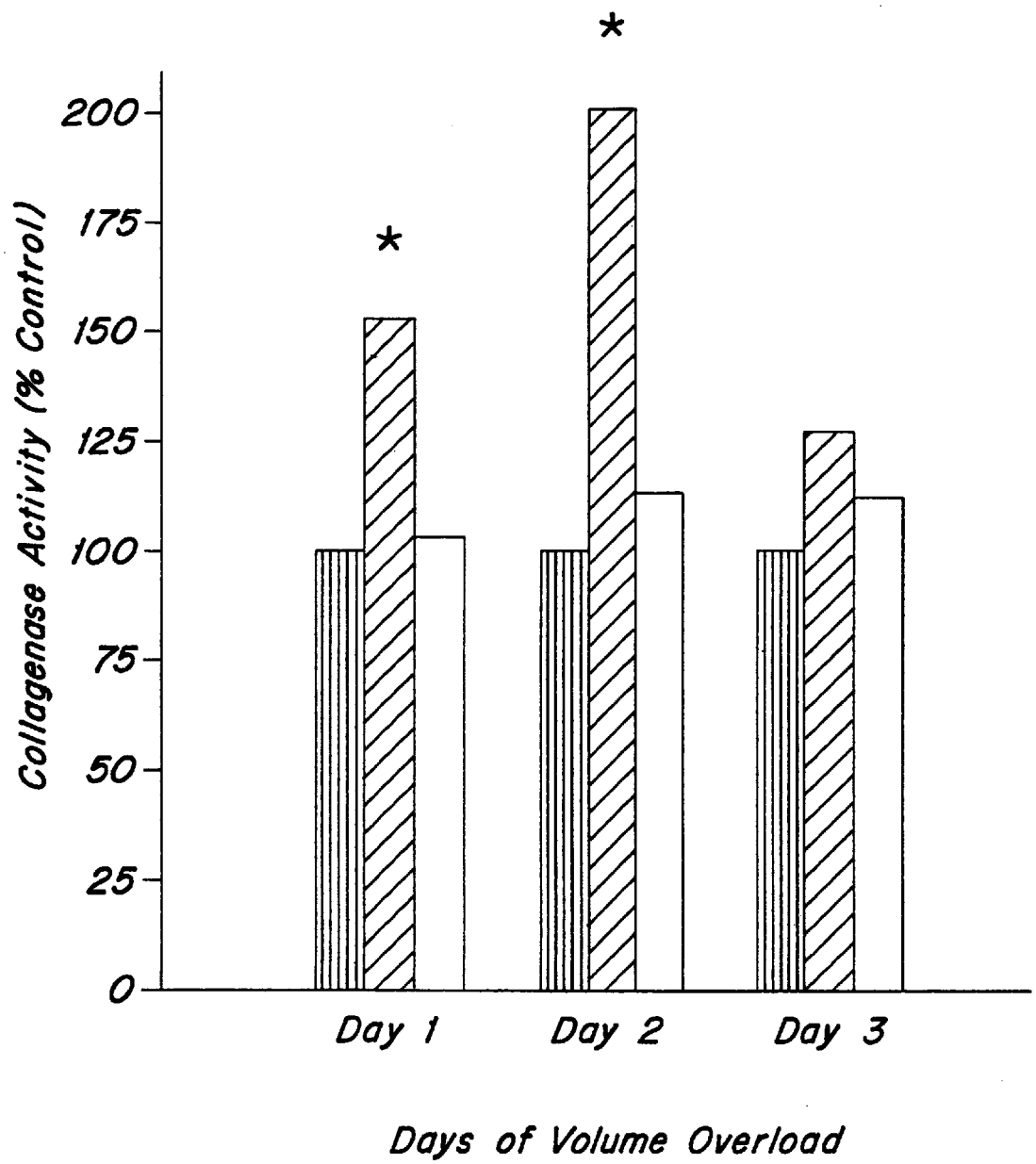

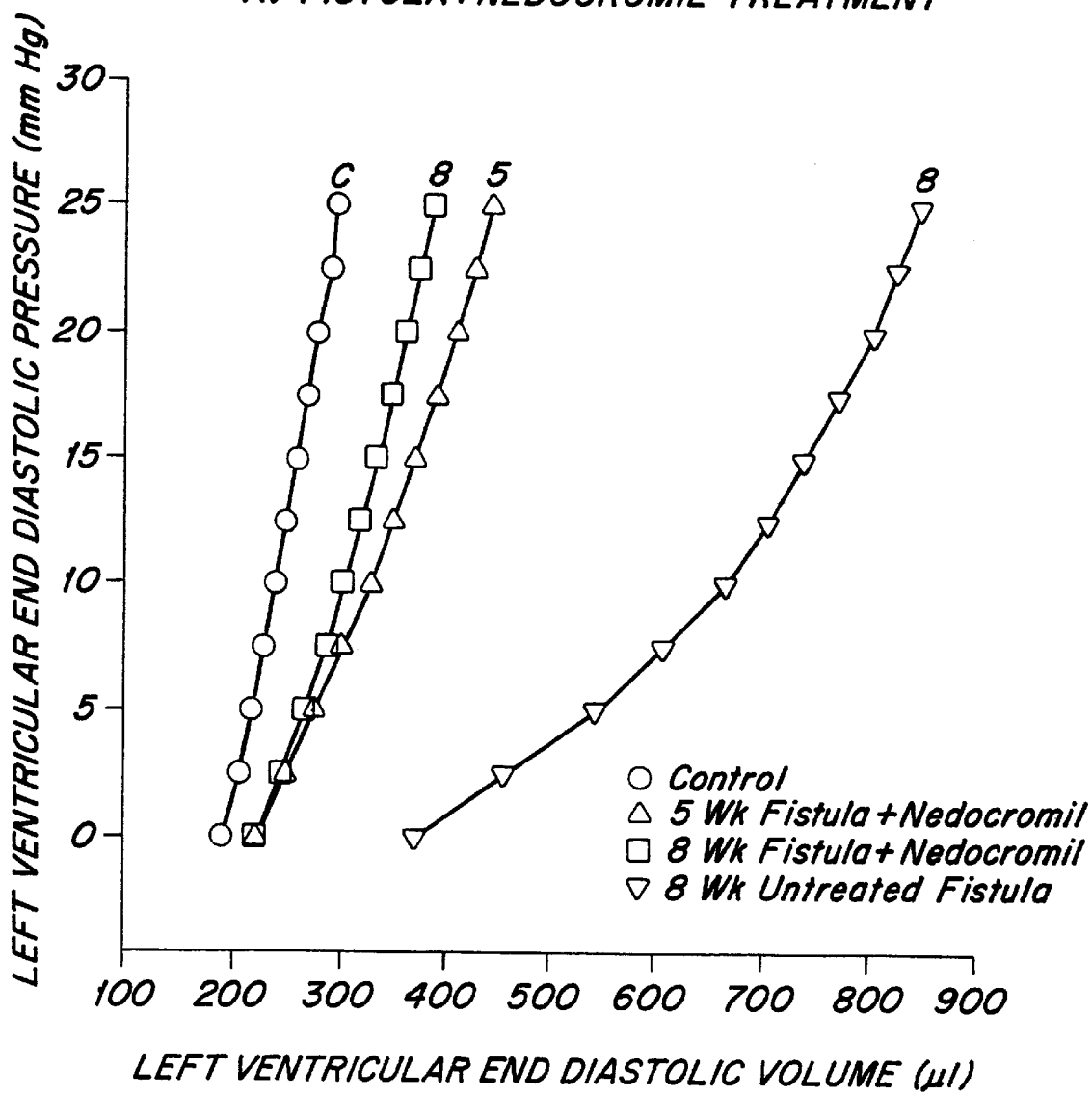

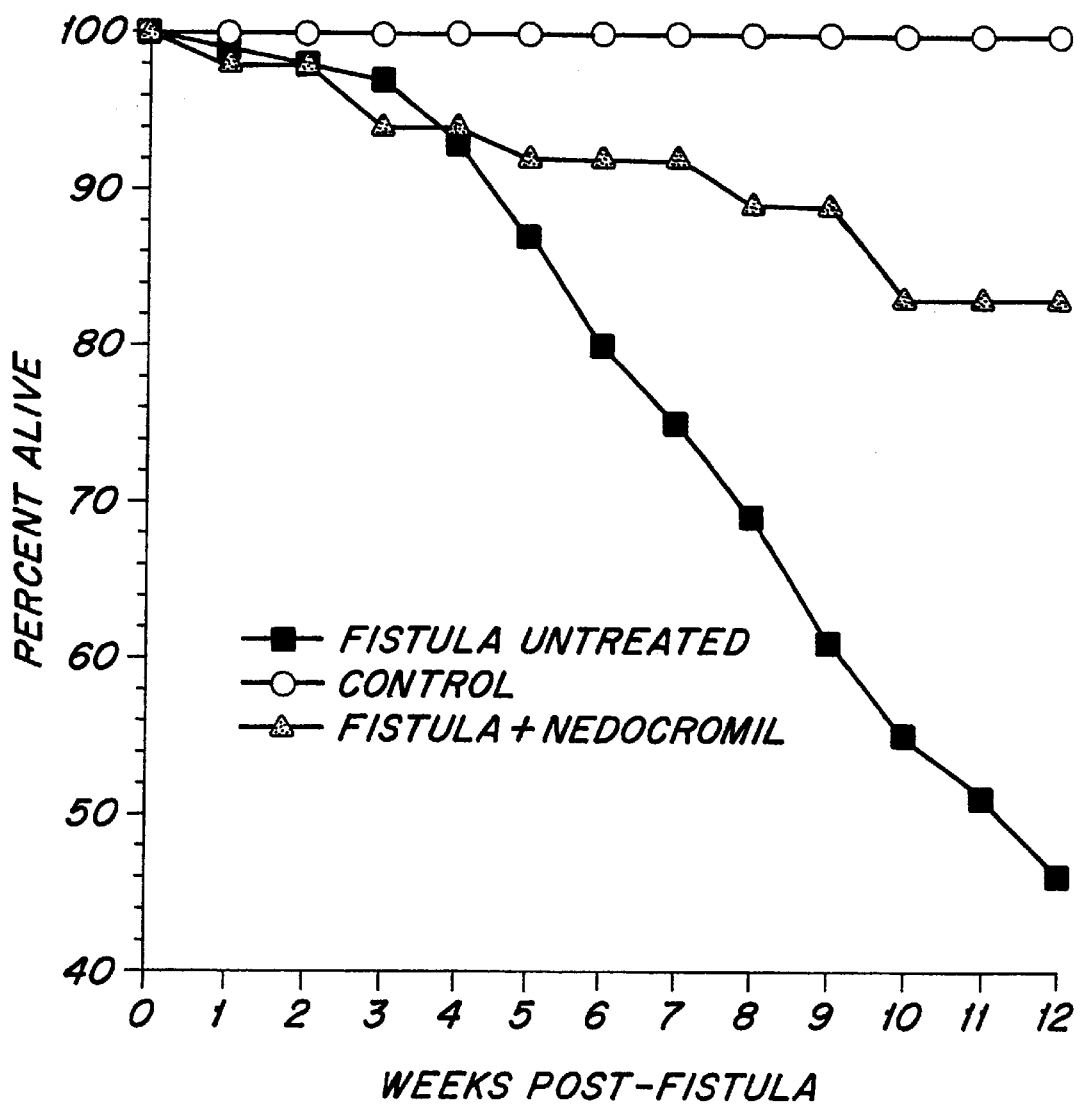

TREATING/PREVENTING HEART FAILURE VIA INHIBITION OF MAST CELL DEGRANULATION

CROSS-REFERENCE TO RELATED APPLICATIONS

This application is a continuation-in-part of our earlier application Ser. No. 09/156,759, filed Sep. 18, 1998, now U.S. Pat. No. 5,952,353, and claiming the priority of copending United States Provisional Patent Application Ser. No. 60/059,568, filed Sep. 19, 1997, each incorporated by reference herein in its entirety and relied upon.

BACKGROUND OF THE INVENTION

1. Technical Field of the Invention

The present invention relates to the treatment or prevention of heart failure by inhibiting mast cell degranulation and, more especially, to a regimen for the pharmacological inhibition of adverse ventricular remodeling and development of heart failure via administration of mast cell stabilizing active species.

2. Description of the Prior Art

It is known to the art that a direct relationship exists between collagenase activity and the number of cardiac mast cells.

Too, the mast cell enzymes trypsin and stromelysin have been shown to activate latent interstitial collagenase in skin, producing extracellular matrix degradation.

Cf. Estensen, "What is the Role of Myocardial Mast Cells," *Human Pathol.*, 16, No. 6, pp. 536–538 (1985); Kovanen et al., "Infiltrates of Activated Mast Cells at the Site of Coronary Atheromatous Erosion or Rupture in Myocardial Infarction," *Circulation*, 92, No. 5, pp. 1084–1088 (1995).

Human heart mast cells have also been characterized in Patella et al., "Human Heart Mast Cells, Isolation, Purification, Ultrastructure and Immunologic Characterization," *J. Immunol.*, 154, pp. 2855–2865 (1995), and in Patella et al., "Immunologic and non-immunologic release of histamine and tryptase from human heart mast cells," *Inflamma. Res.*, 44, Supp. I: S22–S23 (1995).

And "Activation of precursors for matrix metalloproteinases 1 (interstitial collagenase) and 3 (stromelysin) by rat mast-cell proteinases I and II" is described in Suzuki et al., *Biochem. J.*, 305, pp. 301–306 (1995), as is "Effect of preliminary administration of alpha-tocopherol and intal on the course of experimental myocardial necrosis," *Kardiologia*, 29(4), pp. 94–96 (1989).

The effect of cromolyn sodium on necrosis in the first 4 days following myocardial infarction in rats is described in Amatuni et al., "The Effect of alpha-tocopherol and Intal on heart capillary bed and lipid peroxide oxidation in experimental necrosis of the rat myocardium," *Cor-Vasa.*, 31(6), pp. 500–507 (1989).

SUMMARY OF THE INVENTION

It has now unexpectedly and surprisingly been determined that pharmacological inhibition of myocardial mast cell degranulation prevents ventricular remodeling secondary to chronic blood volume overload and subsequent progression of such volume overloaded hearts to the failure state.

Briefly, the present invention features treating/preventing heart failure by administering to an individual in need of such treatment an effective amount of a mast cell degranulation-inhibiting active compound, to prevent adverse ventricular remodeling, heart failure and death secondary to chronic ventricular volume overload.

BRIEF DESCRIPTION OF THE DRAWINGS

FIG. 1 is two graphs, each reflecting temporal response in right ventricular mast cell number during volume overload;

FIG. 2 is also two graphs, each reflecting temporal response in left ventricular mast cell number during volume overload;

FIG. 3 is a graph indicating the relationship between myocardial collagenase activity and mast cell number following ventricular volume overload;

FIG. 4 is a bar graph showing myocardial mast cell response to physiological volume overload due to pregnancy;

FIG. 5 is a graph plotting the relationship between myocardial collagenase actively and mast cell number during and after pregnancy;

FIG. 6 is a bar graph illustrating the influence of chromolyn on mast cell response to chronic volume overload;

FIG. 7 is a bar graph illustrating the influence of chromolyn on left ventricular collagenase activity;

FIG. 8 is a graph showing LV pressure/volume relationship after varied treatments; and FIG. 9 is a graph indicating survival of rats with chronic volume overload secondary to AV fistula.

DETAILED DESCRIPTION OF BEST MODE AND SPECIFIC/PREFERRED EMBODIMENTS OF THE INVENTION

More particularly according to the present invention, it has now been determined that enzymes released by mast cell degranulation initiate myocardial remodeling. Thus, the effect of inhibition of mast cell degranulation on left ventricular (LV) remodeling was demonstrated in a model of chronic volume overload which progresses to overt congestive heart failure. Untreated rats with an infrarenal aortocaval fistula (FISTU) were compared to rats with a fistula treated with nedocromil sodium (FISTCROM, 30 mg/kg/day), and unoperated, untreated controls at 8 weeks post fistula. LV pressure volume relationships were obtained from isolated, blood perfused hearts, and then the ventricles were separated and weighed. In the FISTU group, the chronic volume overload resulted in significant ($p < 0.05$) LV hypertrophy (192%), dilatation (172%), and increased compliance (257%) relative to controls. In marked contrast, treatment with nedocromil consistently prevented the increases in ventricular size and compliance. LV hypertrophy, although attenuated in the FISTCROM group (130%), remained significantly increased ($p < 0.05$) relative to controls. Accordingly, myocardial mast cell degranulation mediates the LV dilatation and progressive decrease in ventricular stiffness occurring in this model. Indeed, the regimen for using drugs which stabilize mast cell membranes and prevent mast cell degranulation was developed from experimental data evidencing the involvement of mast cells in the ventricular remodeling associated with the development of heart failure.

The initial observation was that the number of mast cells in hearts subjected to chronic volume overload was increased in the right ventricle (FIG. 1) and left ventricle (FIG. 2). Furthermore, there was a positive correlation between the number of mast cells and myocardial matrix metalloproteinase (MMP) activity (FIG. 3). Similar observations were made in (1) a less severe model of chronic volume overload (i.e., pregnancy induced) as demonstrated in FIGS. 4 and 5, and (2) in the hamster model of dilated cardiomyopathic heart failure. These findings indicated that mast cells are involved in the regulation of ventricular remodeling induced by chronic volume overload. Therefore, a set of experiments was conducted in which rats were treated with chromolyn sodium to prevent mast cell degranulation. In this study treatment with cromolyn sodium was shown to prevent the concurrent increase in mast cell number (FIG. 6) and MMP activity (FIG. 7) observed in untreated rats with chronic volume overload induced by infrarenal aorta-vena caval (AV) fistula. In particular, nedocromil sodium, a representative mast cell stabilizing compound, was shown to prevent ventricular remodeling in volume overload. In addition, the increase in myocardial collagenase activity that normally accompanies such volume overload was also greatly attenuated.

Nedocromil sodium, a preferred inhibitor of mast cell degranulation according to the invention, as well as technique for the synthesis and various therapeutic applications thereof, are described, for example, in U.S. Pat. Nos. 3,957, 965, 4,161,516, 4,356,181, 4,590,206, 4,760,072, 4,866,072, 4,918,078, 4,935,244, 5,198,221, 5,248,493, 5,260,306 and 5,356,631.

Another preferred inhibitor of mast cell degranulation according to the invention is the asthma-prophylactic and antiallergic drug ketotifen, a benzocycloheptathiophene having the structural formula:

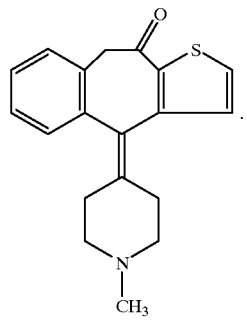

Ketotifen is of especial interest in that, essentially unlike cromolyn sodium and nedocromil sodium, it is more conveniently and efficaciously administered orally. Compare, for example, Craps, *J. Allergy Clin. Immunol.*, pp. 389–393 (August 1985) and references cited therein.

The subject inhibitors of mast cell degranulation are conveniently formulated into any conventional pharmaceutically acceptable vehicle, diluent or carrier therefor.

See also Brower dissertation "Chronic Volume Overload: Contribution Of Ventricular Remodeling To The Pathogenesis Of Heart Failure In Rats," Auburn University, Dec. 14, 1998 (UMI Microform No. 9912907).

In order to further illustrate the present invention and the advantages thereof, the following specific examples are given, it being understood that same are intended only as illustrative and in nowise limitative.

EXAMPLES

Methodology:

All experiments were performed using adult male Sprague Dawley (Hsd:SD) rats housed under standard environmental conditions and maintained on commercial rat chow and tap water ad libitum. All studies conformed with the principles of the National Institutes of Health "Guide for the Care and Use of Laboratory Animals," and the protocol was approved by Auburn University's Animal Care and Use Committee. Anesthesia for surgical procedures and subsequent euthanasia at the experimental endpoint was effected by sodium pentobarbital (50 mg/kg) injected into the intraperitoneal cavity (IP). Post-operative analgesia was provided by buprenorphine HCl (0.05 mg/kg, subcutaneous (SQ) administered to the rats at the time of surgery.

Surgical Preparation:

Infrarenal abdominal aorta-vena cava fistula was created in rats as described in Brower et al., infra. Briefly, a ventral abdominal laparotomy was performed to expose the aorta and caudal vena cava approximately 1.5 cm below the renal arteries. An 18 gauge needle was inserted into the exposed abdominal aorta and advanced through the medial wall into the vena cava to create the fistula. The needle was withdrawn and the ventral aortic puncture sealed with cyanoacrylate. Creation of a successful A-V fistula was visually evident by the pulsatile flow of oxygenated blood into the vena cava. The abdominal musculature and skin incisions were closed by standard techniques with absorbable suture and autoclips. Nedocromil treated groups had time release drug pellets implanted SQ beginning one week prior to the fistula surgery.

Experimental Protocol:

To demonstrate the effectiveness of the regimen according to the present invention, the extent of left ventricular remodeling was determined in groups of sham-operated, age-matched control and rats with an AV fistula which were either untreated or receiving nedocromil sodium at 30 mg $kg^{-1}$ $day^{-1}$ administered subcutaneously via osmotic minipump. Rats were randomly selected from each group and ventricular function was studied at 5 and 8 weeks post-fistula. Prior to sacrifice, the rats were weighed, patency of the fistula was visually confirmed and the hearts were isolated for in vitro functional studies. After completing the functional studies, the atria and great vessels were removed and the left ventricle (LV) and right ventricle (RV) were separated and weighed. Lung wet weight was also obtained after the esophagus and trachea were trimmed away and the pleural surface was blotted dry.

Assessment of Ventricular Size and Function:

LV volume and function were evaluated in vitro using a modified Langendorff isolated heart preparation as previously described in Brower et al., infra. Briefly, the apparatus consisted of a pressurized perfusion reservoir and a collection reservoir connected in circuit with a support rat. Arterial blood from the carotid artery of the support rat was pumped (Masterflex peristaltic pump, Cole-Parmer Instrument Company, Niles, Ill., USA) to a pressurized reservoir for retrograde perfusion of the heart. The coronary venous effluent was collected and returned to the support rat through a jugular vein catheter in order to filter and oxygenate the blood supply to the isolated heart. The temperature of the blood in the perfusion reservoir was maintained at 37±1° C. and the environment around the isolated heart was maintained constant at 35±2° C.

The hearts to be studied were extirpated from anesthetized rats after measurement of the carotid artery blood pressure (MAP). Left ventricular end diastolic pressure (LVEDDP) was not obtained in these rats in order to prevent damage to the aortic valve. Prior to removal of the heart, a cannula was inserted into the aorta at a level just proximal to the first pair of intercostal arteries and secured with a silk ligature. Retrograde perfusion of the coronary arteries with blood from the perfusion reservoir was begun as soon as the cannula was secured. The heart and lungs were quickly removed from the chest and attached to the apparatus. Pressure in the perfusion reservoir was adjusted to equal the in vivo MAP.

Intraventricular volumes and pressures were recorded using a latex balloon inserted through the mitral valve orifice into the LV. Once the heart developed stable isovolumetric contractions, the balloon volume which produced an LVEDP of 0 mm Hg ($V_o$) was determined. Balloon volume was then increased in 20 µl increments from this point until an LVEDP of 25 mm Hg was attained. The end diastolic and peak isovolumetric pressures were recorded following each increase in balloon volume.

Morbidity and Mortality Assessment:

To determine the temporal pattern of heart failure in this model, 100 untreated rats with chronic A-V fistula were evaluated weekly for signs of congestive heart failure. For the purpose of this study, overt congestive heart failure is defined as a significant increase in body weight (i.e., $\geq 50$ grams in a 7–10 day period) together with labored respiration, pulmonary edema, abdominal ascites, and/or pitting edema. The experimental end point was the development of overt congestive heart failure or sudden death. The percentage of rats succumbing to sudden death or developing heart failure was computed by dividing the number of affected rats by the number of rats in the study for that evaluation period.

Results:

The increased workload imposed on the heart by a sustained volume overload induces compensatory cardiomyocyte hypertrophy, increased LV compliance, and ventricular dilatation (Brower et al., "Temporal evaluation of left ventricular remodeling and function in rats with chronic volume overload," Am. *J. Physiol. Heart Circ. Physiol.*, 271 (5), H2071–H2078 (1996)). As indicated in that study, an early and progressive myocardial hypertrophy and ventricular dilatation occurred in response to a biventricular volume overload induced by infrarenal AV fistula. There was also a sustained increase in in vivo left ventricular end diastolic pressure (LVEDP), with the peak increase in LVEDP at 3 weeks corresponding to the subsequent development of further LV dilatation and a significant decrease in LV stiffness at 5 weeks post-A-V fistula. Findings consistent with the development of decompensated ventricular function were also identified in approximately 50% of the 8 week post-A-V fistula rats. Subsequently determined were the LV mass, volume, stiffness, and function of hearts from rats with chronic A-V fistula for periods of 14 and 20 weeks. These findings demonstrate progressive decompensation leading to overt heart failure and death secondary to sustained chronic volume overload (e.g., mortality $\geq 85\%$ at 20 weeks and 100% at 32 weeks postfistula). However, the development of depressed ventricular function and congestive heart failure in the A-V fistula groups was not associated with further increases in LV size, mass, and compliance.

To date, rats receiving nedocromil sodium have been evaluated at 5 and 8 weeks. As shown in FIG. 8, treatment with nedocromil consistently prevented the increases in ventricular size and compliance. Therefore, it has been shown that myocardial mast cell degranulation mediates the LV dilatation and progressive increase in ventricular compliance seen in the untreated fistula groups. As can be seen from FIG. 9, the ability of nedocromil to prevent adverse ventricular remodeling translates into a beneficial effect of mortality due to heart failure. That is, at 12 weeks 83% of the rats receiving nedocromil were alive versus only 46% of the untreated rats. Thus, the ability of a mast cell stabilizer class of drugs (e.g., nedocromil sodium and cromolyn sodium) to prevent adverse myocardial remodeling (i.e., ventricular dilatation, sphericalization, and wall thinning) and to significantly improve mortality associated with a sustained ventricular volume overload reflects the effectiveness of this class of drugs for the prevention of human heart failure regardless of etiology.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regimen for preventing/treating heart failure, comprising administering to an individual in need of such treatment the mast cell degranulation inhibitor ketotifen in an amount effective to prevent adverse myocardial remodeling secondary to sustained blood volume overload.

2. The regimen as defined by claim 1, comprising orally administering said effective amount of ketotifen to said individual.

3. The regimen as defined by claim 1, carried out for such period of time as to continuously elicit the desired therapeutic effect.

* * * * *